US 10,494,593 B2

United States Patent
Ejiri et al.

(10) Patent No.: US 10,494,593 B2
(45) Date of Patent: Dec. 3, 2019

(54) CULTURE CHAMBER AND CULTURE METHOD

(71) Applicants: KURARAY CO., LTD., Kurashiki-shi (JP); PUBLIC UNIVERSITY CORPORATION YOKOHAMA CITY UNIVERSITY, Yokohama-shi (JP)

(72) Inventors: Yoko Ejiri, Tsukuba (JP); Satoru Ayano, Tsukuba (JP); Naoto Fukuhara, Tsukuba (JP); Hideki Taniguchi, Yokohama (JP); Takanori Takebe, Yokohama (JP)

(73) Assignees: CORNING INCORPORATED, Corning, NY (US); PUBLIC UNIVERSITY CORPORATION YOKOHAMA CITY UNIVERSITY, Yokohama-shi, Kanagawa (JP)

( * ) Notice: Subject to any disclaimer, the term of this patent is extended or adjusted under 35 U.S.C. 154(b) by 70 days.

(21) Appl. No.: 14/896,251

(22) PCT Filed: Jun. 5, 2014

(86) PCT No.: PCT/JP2014/002993
§ 371 (c)(1),
(2) Date: Dec. 4, 2015

(87) PCT Pub. No.: WO2014/196204
PCT Pub. Date: Dec. 11, 2014

(65) Prior Publication Data
US 2016/0137962 A1    May 19, 2016

(30) Foreign Application Priority Data
Jun. 7, 2013    (JP) .................................. 2013-120915

(51) Int. Cl.
*C12M 1/32* (2006.01)
*C12M 1/24* (2006.01)

(52) U.S. Cl.
CPC ............ *C12M 23/08* (2013.01); *C12M 23/12* (2013.01)

(58) Field of Classification Search
CPC ..................................................... C12M 23/12
See application file for complete search history.

(56) References Cited

U.S. PATENT DOCUMENTS

2008/0227664 A1* 9/2008 Honma .................. C12M 23/12
506/39
2010/0221768 A1* 9/2010 Akai ...................... C12M 23/10
435/29

(Continued)

FOREIGN PATENT DOCUMENTS

JP    H08-131153 A    5/1996
JP    2001-509272 A   7/2001

(Continued)

OTHER PUBLICATIONS

Combined Office Action and Search Report dated Aug. 5, 2016 in Chinese Patent Application No. 201480032635.8 (with partial English translation and English translation of Categories of Cited Documents).

(Continued)

*Primary Examiner* — Jonathan M Hurst

(57) ABSTRACT

A culture chamber includes a plurality of recesses (10) each formed of a bottom portion (11) and an opening portion (12). The bottom portion (11) has a hemispherical shape and the opening portion (12) is defined by a wall that surrounds an area from a boundary between the opening portion (12) and the bottom portion (11) to an end of each of the recesses (10), the wall having a taper angle in a range from 1 degree to 20 degrees. An equivalent diameter of the boundary is in (Continued)

a range from 50 μm to 2 mm and a depth from a bottom of the bottom portion (11) to the end of each of the recesses is in a range from 0.6 or more times to 3 or less times the equivalent diameter, and the wall defining the opening portion (12) forms a surface continuous to the bottom portion (11).

15 Claims, 14 Drawing Sheets

(56) References Cited

U.S. PATENT DOCUMENTS

| | | | |
|---|---|---|---|
| 2011/0165609 A1* | 7/2011 | Ramsing | C12M 21/06 435/29 |
| 2013/0122580 A1* | 5/2013 | Tsukada | C12M 23/12 435/289.1 |
| 2013/0203159 A1 | 8/2013 | Itoh et al. | |
| 2014/0011269 A1 | 1/2014 | Sakura et al. | |
| 2014/0227784 A1 | 8/2014 | Ejiri et al. | |

FOREIGN PATENT DOCUMENTS

| | | |
|---|---|---|
| JP | 2005-27598 A | 2/2005 |
| JP | 2010-088347 A | 4/2010 |
| WO | 98/31466 | 7/1998 |
| WO | 2008/130025 A1 | 10/2008 |
| WO | 2012/036011 A1 | 3/2012 |
| WO | WO 2012/133514 A1 | 10/2012 |
| WO | 2013/042360 | 3/2013 |

OTHER PUBLICATIONS

Search Report and Written Opinion dated Sep. 26, 2016 in Singaporean Patent Application No. 11201509870Q.
Extended European Search Report dated Dec. 2, 2016 in Patent Application No. 14808113.6.
Juergen Friedrich, et al., "Spheroid-based drug screen: considerations and practical approach," Nature Protocols, vol. 4, No. 3,Feb. 12, 2009, pp. 309-324.
Franziska Hirschhaeuser, et al., "Multicellular tumor spheroids: An underestimated tool is catching up again," Journal of Biotechnology, No. 148, 2010, pp. 3-15.
Celine Liu Bauwens, et al., "Control of Human Embryonic Stem Cell Colony and Aggregate Size Heterogeneity Influences Differentiation Trajectories," Stem Cells, 2008, pp. 2300-2310.
International Search Report dated Sep. 9, 2014 in PCT/JP14/02993 Filed Jun. 5, 2014.
Office Action dated Oct. 10, 2017 in Japanese Patent Application No. 2015-521306 (with unedited computer-generated English translation).
Written Opinion dated Sep. 26, 2017 in Singaporean Patent Application No. 11201509870Q.
Curcio et al. "mass transfer and metabolic reations in hepatocyte speroids cultureed in rotating wall gas-permeable membrane system" Biomaterials 28 (2007) pp. 5487-5497.

* cited by examiner

CULTURE CHAMBER AND CULTURE METHOD

TECHNICAL FIELD

The present invention relates to culture of cells and harvesting of the cells.

BACKGROUND ART

Along with the recent development of cell technology, new culture methods to obtain cells having a function similar to an in-vivo function by mimicking an in-vivo pericellular environment or morphology have been developed. An attempt has been made to use cells cultured by such methods as a simulator for treatment or biological reaction. Various culture methods have been developed, such as a method of culturing cells using a culture support composed of a sponge or fiber; a suspension culture method in which cells are suspended in a medium so that the cells spontaneously form a spheroid; and a method of culturing cells to form a spheroid by performing a cell non-adhesion treatment on a conventional culture chamber (a flask or the like). In particular, a spheroid culture is an excellent method by which interactions of cells can be maintained, and thus the method is applied to various cells such as pancreatic islet cells, liver cells, stem cells, and cancer cells. In recent years, studies focusing on the size of a spheroid have been made. For example, in a drug screen test using cancer cells, the diameter or volume of a spheroid is used as an index (Non Patent Literature 1). It is also disclosed that cells have different functions depending on the size of a spheroid (Non Patent Literature 2 and 3). In addition to the technique of forming a spheroid as mentioned above, a technique of controlling the size of a spheroid has attracted attention. Further, since it is possible to reproduce a specific function of a cell, it is expected that this technique of controlling the size of a spheroid will be applicable in various fields, for example, the artificial organ and bioreactor fields. In such applications, a technique of preparing a large number of spheroids and recovering the spheroids is important.

As means for creating a spheroid having a uniform diameter, Patent Literature 1 discloses a method of controlling the size of each spheroid formed by changing the number of cells to be seeded in a 96WP with a U-shaped bottom on which a hydrophilic membrane is formed. However, the number of spheroids per culture area is small, and thus it is difficult to prepare a large number of spheroids. As other methods for creating a spheroid having a uniform diameter, Patent Literature 2 to 4 disclose methods of forming a spheroid in a micro-space.

CITATION LIST

Patent Literature

[Patent Literature 1] Japanese Unexamined Patent Application Publication No. H08-131153
[Patent Literature 2] Japanese Unexamined Patent Application Publication No. 2010-88347
[Patent Literature 3] International Patent Publication No. WO 2012/036011
[Patent Literature 4] International Patent Publication No. WO 2013/042360

Non Patent Literature

[Non Patent Literature 1] Juergen Friedrichl, et al., "Spheroid-based drug screen: considerations and practical approach", PROTOCOL, Feb. 12, 2009 (Published online) pp. 309-324
[Non Patent Literature 2] Franziska Hirschhaeuser, et al., "Multicellular tumor spheroids: An underestimated tool is catching up again", Journal of Biotechnology 148, 2010, pp. 3-15
[Non Patent Literature 3] C'ELINE LIU BAUWENS, et al., "Control of Human Embryonic Stem Cell Colony and Aggregate Size Heterogeneity Influences Differentiation Trajectories", STEM CELL, 2008, pp. 2300-2310

SUMMARY OF INVENTION

Technical Problem

However, in the culture method disclosed in Patent Literature 1, the culture efficiency is extremely low, which is a rate-limiting step for the large-scale culture. In the culture methods disclosed in Patent Literature 2 and 3, the efficiency of formation of spheroids per unit area is high, but there is a possibility that the spheroids will be removed from the inside of the culture space during replacement of the medium. Accordingly, careful attention is required during replacement of the medium. Moreover, a study has been made on a method of causing a part of a spheroid to adhere to the inside of a micro-space so as to prevent removal of the spheroid (Patent Literature 4). However, since adhesion property is different in each type of cell, it is necessary to consider a surface treatment method for each of the cells to be used, and thus the method is impractical.

The present invention has been made in view of the above-mentioned background. An object of the present invention is to design a micro-space structure which facilitates replacement of a medium and harvesting of cells, and to provide a culture chamber having the said micro-space structure, and a culture method using the said culture chamber, to make it possible to prepare spheroids with a uniform size with high efficiency, or to prepare a large number of spheroids with a uniform size with high efficiency.

Solution to Problem

According to an aspect of the present invention, a culture chamber according to one embodiment includes a plurality of recesses each formed of a bottom portion and an opening portion. The bottom portion has one of a hemispherical shape and a truncated cone shape. The opening portion is defined by a wall that surrounds an area from a boundary between the opening portion and the bottom portion to an end of each of the recesses, the wall having a taper angle in a range from 1 degree to 20 degrees. In addition, an equivalent diameter of the boundary is in a range from 50 µm to 2 mm and a depth from a bottom of the bottom portion to the end of each of the recesses is in a range from 0.6 or more times to 3 or less times the equivalent diameter. The wall defining the opening portion forms a surface continuous to the bottom portion, and an inclination of the continuous surface changes at the boundary.

In the culture chamber according to one embodiment, it is preferable that the end of each of the recesses have one of a hemispherical shape, a trapezoidal shape, and an inverted triangular shape. It is also preferable that an area between two adjacent recesses be flat and a distance between the two recesses be in a range from 5 µm to 50 µm.

Further, in the culture chamber according to one embodiment, it is preferable that the culture chamber be a resin molding formed of one or a combination of two or more selected from the group consisting of acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, and silicon resin. It is preferable that a functional group be formed on the recesses by a surface modification treatment method of any one of plasma treatment, glass coating, corona discharge, and UV ozonation, or a combination thereof and the treatment be performed so that a water contact angle becomes 45 degrees or less.

It is preferable that a hydrophilic polymer chain that inhibits cell adhesion be immobilized in the recesses.

It is preferable that a phospholipid or a phospholipid-polymer complex be immobilized in the recesses.

It is preferable that the recesses each have a cell non-adhesive surface on which at least one polymer of a hydrophilic polymer chain that inhibits cell adhesion, and a phospholipid, or a phospholipid-polymer complex is immobilized after a functional group is formed in the recesses by a surface modification treatment method of any one of plasma treatment, glass coating, corona discharge, and UV ozonation, or a combination thereof and the treatment is performed so that a water contact angle becomes 45 degrees or less.

It is preferable that hydrophilic polymer chain be poly (hydroxyethyl methacrylate), and it is more preferable that an average molecular weight of the poly(hydroxyethyl methacrylate) be 100,000 or more.

According to an aspect of the present invention, a culture method according to one embodiment uses any one of the culture chambers described above. This culture method includes: dispersing cells into a medium, a total number of the cells being equal to or greater than a number (N) of the recesses of the culture chamber and equal to or less than a number obtained by multiplying the number (N) of the recesses by a value obtained by dividing a volume (V1) of a space defined by each of the recesses by a volume (V2) of cells to be seeded; and adding the medium to the culture chamber.

In one aspect of the culture method according to an embodiment of the present invention, it is preferable that one spheroid be formed in one space defined by each of the recesses, and it is more preferable that a spheroid be formed in the space and the spheroid is allowed to grow (proliferate).

In the case of differentiating and inducing a spheroid, the spheroid is preferably induced in a state where the spheroid is formed in the space.

It is preferable that 60% or more of a total number of spheroids formed in the culture chamber have a diameter in a range of ±5% of an average spheroid diameter.

It is preferable that cells in the recesses be recovered by agitating the medium, and it is more preferable that the agitation of the medium be done by any one of the following means: agitation of the medium by shaking the culture chamber; agitation of the medium by sucking and discharging the medium; agitation of the medium by disposing a stirring blade in the culture chamber; and agitation of the medium by placing a stirrer in the culture chamber, or a combination thereof.

It is preferable that the medium be replaced at least once and 20% or more of the medium be replaced.

According to another aspect of the present invention, a culture method according to one embodiment uses any one of the culture chambers described above. The culture method for cell seeding, cell culture, replacement of a medium, and harvesting of cells includes the steps of:

a) dispersing cells into a medium, the number of the cells being equal to or greater than a number (n) of recesses of the culture chamber and equal to or less than a number obtained by multiplying the number (n) of the recesses by a value obtained by dividing a volume (V) of each of the recesses by a volume (v) of cells to be seeded, and adding the medium to the culture chamber;

b) culturing the cells in the culture chamber for 12 hours or more to form a spheroid;

c) sucking 20% or more of the medium and then injecting the same amount of fresh medium;

d) repeating the steps a) to c) a plurality of times to allow the spheroid to grow;

e) allowing the spheroid to grow to a desired size and then agitating the medium to suspend the cells within the recesses in the medium; and f) sucking the medium including the cells by a suction machine to recover the cells.

Advantageous Effects of Invention

According to the present invention, it is possible to provide a culture chamber capable of preparing a large number of spheroids with a uniform size with high efficiency and having a micro-space structure which is designed to enable replacement of a medium and harvesting of cells, and a culture method using the culture chamber.

DESCRIPTION OF EMBODIMENTS

Figure 1:
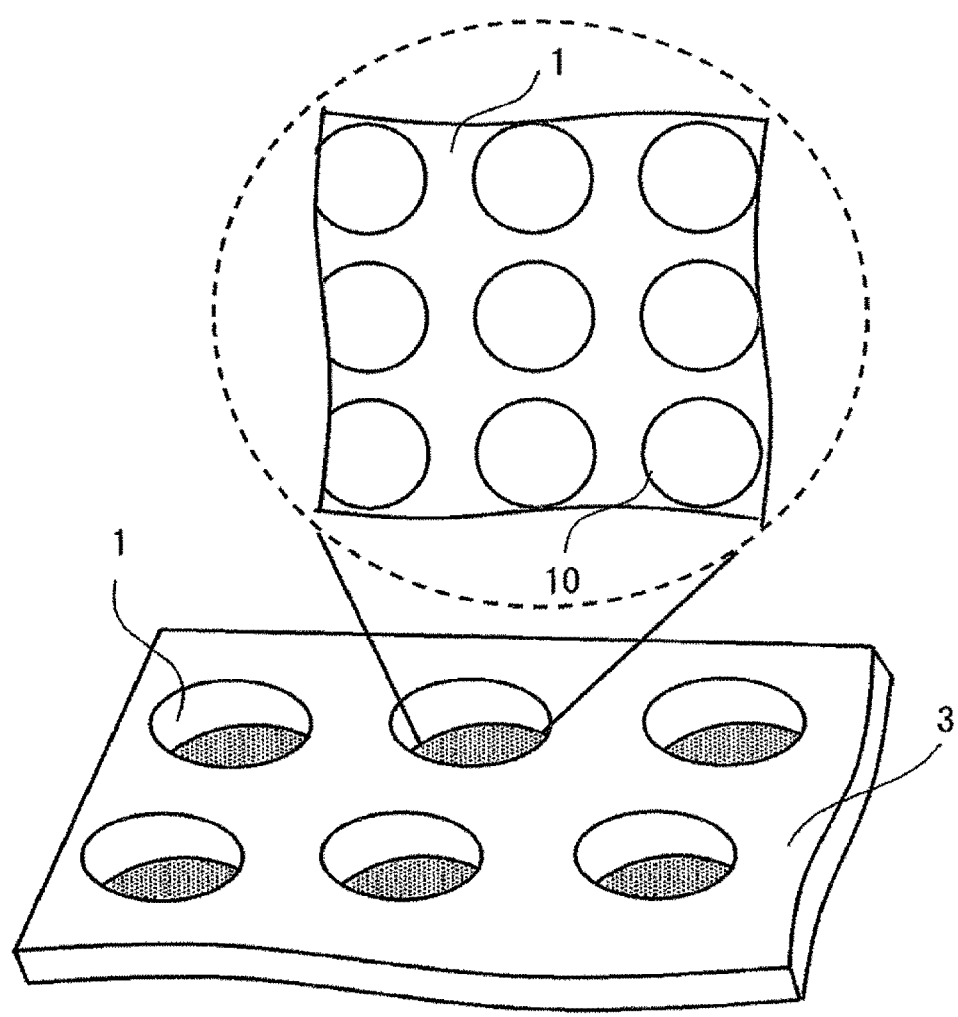
FIG. 1 is a diagram showing an example of a culture chamber according to an embodiment.

Embodiments will be described below with reference to the drawings. To clarify the explanation, omissions and simplifications are made as necessary in the following description and the drawings. Throughout the drawings, the constituent elements having the same configuration or function, or corresponding parts are denoted by the same reference numerals, and the descriptions thereof are omitted.

First Embodiment

<Culture Chamber>

FIG. 1 is a diagram showing an example of a culture chamber according to an embodiment. FIG. 1 shows a part of a culture plate 3 including a plurality of culture chambers 1. FIG. 1 shows a part of a culture plate 3 including a plurality of culture chambers 1. The upper part of FIG. 1 shows some of a plurality of recesses 10 which are formed in the bottom of each of the culture chambers 1, when viewed from the top of the culture plate 3. The plurality of recesses 10 are arranged in each of the culture chambers 1. In terms of the production of the culture chambers 1 and the efficiency of cell culture, it is preferable to arrange the plurality of recesses 10 in a regular manner. One culture chamber 1 corresponds to, for example, one well arranged in a plate including a plurality of wells. In other words, the plurality of recesses 10 are arranged in the respective wells of a well plate.

A well plate is an experimental/testing instrument formed of a flat plate having a number of dents (holes or wells), and each well is used as a test tube or a petri dish. The number of wells is, for example, 6, 24, 96, 384, or more. Examples of the shape of the bottom of each well include a flat shape, a round shape, and a combination of a number of elongated microtubes (deep well plate).

Each recess 10 forms a micro-space, which is a small space for culture of cells, and thus each recess can also be referred to as a microchamber.

Figure 2:
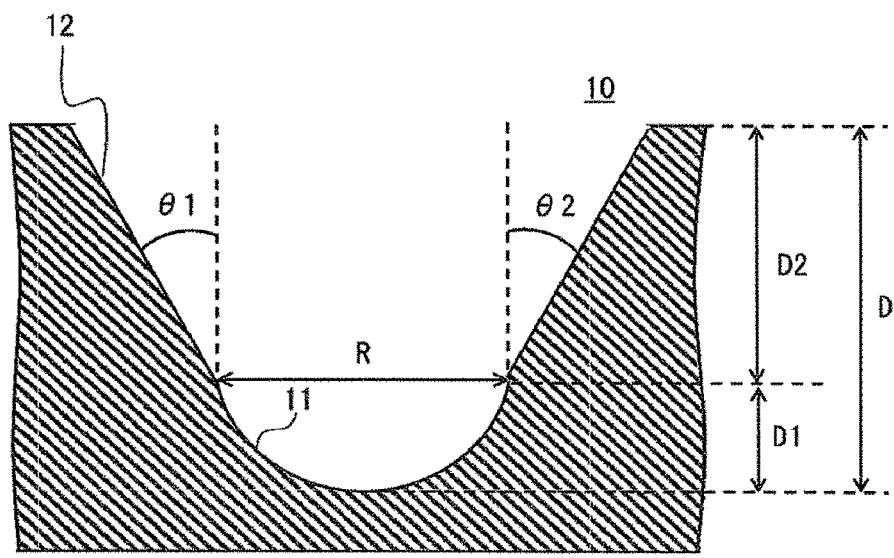
FIG. 2 is a cross-sectional view showing an example of the shape of a recess according to a first embodiment.
Figure 3:
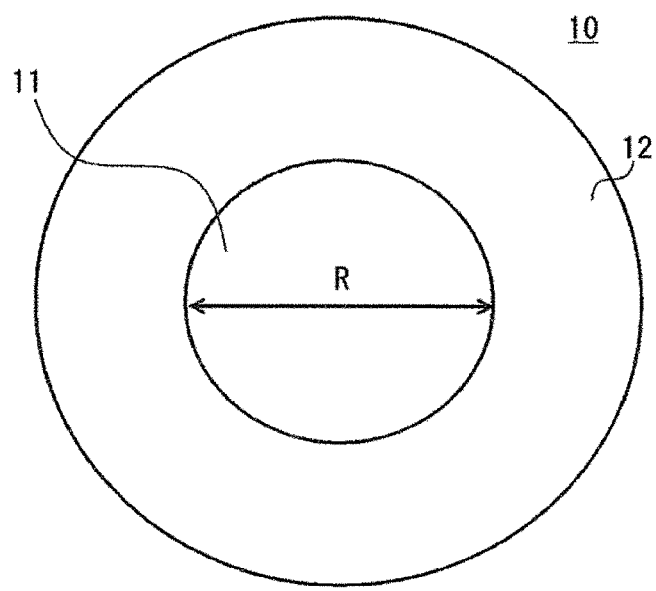
FIG. 3 is a top view showing an example of the shape of the recess according to the first embodiment.

FIGS. 2 and 3 show an example of the shape of a recess according to a first embodiment. FIG. 2 shows a cross-sectional view of one recess 10, and FIG. 3 shows a top view of one recess 10. The recess 10 shown in FIG. 3 is an example of the detailed structure of each of the recesses 10 shown in the upper part of FIG. 1.

Each recess 10 is composed of a bottom portion 11 and an opening portion 12. The bottom portion 11 is a portion serving as the bottom of the culture chamber 1, and the opening portion 12 is a portion disposed above the bottom portion 11. A portion where the bottom portion 11 and the opening portion 12 are in contact is referred to as a boundary. In FIG. 2, a portion whose length is indicated by an arrow "R" corresponds to the location of the boundary. In FIG. 3, the boundary location is indicated by a double dashed chain line. Note that the bottom portion 11 and the opening portion 12 are formed of a continuous surface and are produced in an integrated manner.

FIGS. 2 and 3 show an equivalent diameter R and a depth (height) H of each of the plurality of recesses 10 formed in the culture chamber 1.

The term "equivalent diameter R" refers to the diameter of a circle inscribed in the bottom portion 11 of each recess 10. In this case, the equivalent diameter R is the diameter of an inscribed circle that is inscribed at the boundary between the bottom portion 11 and the opening portion 12. More specifically, the equivalent diameter R is the diameter of a circle inscribed in a shape of a plane that is perpendicular to the direction of the height H of each recess 10 at the boundary.

The term "depth D" refers to a length from the bottom on the inside of the bottom portion 11 to an upper end of each recess 10. The upper end of the recess 10 corresponds to an end (upper end) of the opening portion 12. The depth D corresponds to the depth of a space formed by the recess 10. In other words, the depth D is a depth from the bottom of a space, which is formed by the bottom portion 11, to an upper end of a space formed by the opening portion 12. FIG. 2 shows not only the depth D of the recess 10, but also a depth D1 of the bottom portion 11 and a depth D2 of the opening portion 12.

The bottom portion 11 forms a space (first space) in which cells are cultured. The bottom portion 11 has, for example, a hemispherical shape. For example, a shape obtained by dividing a spherical shape having the equivalent diameter R as a diameter into halves can be used. The shape of the bottom portion 11 is not limited to a hemispherical shape. Other specific examples of the shape will be described in a second embodiment.

The opening portion 12 forms a space (second space) that operates to support culture and harvesting of cells. The opening portion 12 is formed of a wall which surrounds an area from a boundary between the opening portion 12 and the bottom portion 11 to an end (tip) of the recess 10 and which has a taper angle in a range from 1 degree to 20 degrees. The taper angle of the wall constituting the opening portion 12 is preferably in a range from 5 degrees to 15 degrees, and more preferably, 10 degrees. This is because if the taper angle is extremely small, it is difficult to transfer cells from the recesses into a medium during harvesting of the cells, and if the taper angle is extremely large, the cells are removed during replacement of the medium.

Taper angles are represented by $\theta 1$ and $\theta 2$ in FIG. 2. In an example of the shape of each recess 10 shown in FIGS. 2 and 3, the taper angles $\theta 1$ and $\theta 2$ are substantially the same.

The boundary between the bottom portion 11 and the opening portion 12 is formed in such a manner that the equivalent diameter R is in a range from 50 μm to 1 mm. To supply nutrients to a central portion of a spheroid, the equivalent diameter is preferably in a range from 50 μm to 500 μm, and more preferably, in a range from 100 μm to 500 μm. This is because it is said that nutrients and oxygen are transferred into cells only by diffusion and a central portion of a spheroid with a size of 300 μm or less does not become necrotic (Efrem Curcio et al., "Mass transfer and metabolic reactions in hepatocyte spheroids cultured in rotating wall gas-permeable membrane system", Biomaterials 28 (2007) 5487-5497). Accordingly, the above-mentioned diameter range is preferable to prevent a spheroid from growing to the size of 300 μm.

On the contrary, when it is intended to cause necrosis in a central portion of a cell, like in a cancer cell (Franziska Hirschhaeuser et al., "Multicellular tumor spheroids: An underestimated tool is catching up again", Journal of Biotechnology 148 (2010) 3-15, FIG. 1), the equivalent diameter R is preferably equal to or more than 400 μm and less than 2 mm. This is because, as mentioned above, nutrients can be transferred to a central portion of a spheroid with a size of 300 μm, so that necrosis does not occur. Accordingly, in order to obtain a spheroid having a diameter of 300 μm or more, it is necessary that the equivalent diameter be equal to or more than 400 μm.

In addition, the depth D from the bottom of the bottom portion to the end of each of the recesses is set in a range from 0.6 or more times to 3 or less times the equivalent diameter R. The depth D is preferably in a range from 0.7 or more times to 1.2 or less times the equivalent diameter R, and more preferably, in a range from 0.8 to 1 times the equivalent diameter R.

In each culture chamber 1, the area between two adjacent recesses 10 is preferably flat. For example, the distance between two recesses 10 is preferably in a range from 5 μm to 50 μm.

This is because it is preferable to increase the number of spheroids per unit area and culture the spheroids at a high density so that a large number of spheroids can be efficiently obtained. To achieve this, the area of the upper surface of the wall on which no spheroid is formed is preferably small as much as possible. In this case, however, when the taper angle is small and the wall is thin, cracking may easily occur due to a vibration during cell seeding or replacement of a medium. Accordingly, the distance between two recesses is preferably 5 μm or more. In view of this, the distance between two recesses is preferably in a range from 5 to 20 μm.

On the other hand, the two adjacent recesses 10 may come into contact with each other. For example, a part of an end of one of the two recesses 10 and a part of an end of the other one of the two recesses 10 may come into contact with each other, so that the inclined surfaces of the opening portions 12, each of which forms a taper angle, may come into contact with each other to form a chevron shape.

The culture chamber 1 having the above-described shape is preferably produced in the following manner.

Each culture chamber 1 is preferably a resin molding formed of one or a combination of two or more selected from the group consisting of acrylic resin, polylactic acid, polyglycolic acid, styrene resin, acrylic styrene copolymer resin, polycarbonate resin, polyester resin, polyvinyl alcohol resin, ethylene vinyl alcohol copolymer resin, thermoplastic elastomer, vinyl chloride resin, and silicon resin.

A functional group is preferably formed on the recesses 10 of the culture chamber 1 by a surface modification treatment method of any one of plasma treatment, glass coating, corona discharge, and UV ozonation, or a combination thereof and the treatment is preferably performed so that the water contact angle becomes 45 degrees or less.

In addition, a hydrophilic polymer chain that inhibits cell adhesion is preferably immobilized in the recesses 10. More preferably, the hydrophilic polymer chain is immobilized in the recesses 10 that are treated so that the above-mentioned water contact angle becomes 45 degrees or less.

Furthermore, a phospholipid or a phospholipid-polymer complex is preferably immobilized in the recesses 10. More preferably, this immobilization treatment is performed on each recess 10 that is treated so that the above-mentioned water contact angle becomes 45 degrees or less, each recess 10 in which a hydrophilic polymer chain is immobilized, or a combination of these recesses 10.

Moreover, each of the recesses 10 preferably has a cell non-adhesive surface on which at least one polymer of a hydrophilic polymer chain that inhibits cell adhesion, and a phospholipid, or a phospholipid-polymer complex is immobilized after a functional group is formed in the recesses by a surface modification treatment method of any one of plasma treatment, glass coating, corona discharge, and UV ozonation, or a combination thereof and the treatment is performed so that the water contact angle becomes 45 degrees or less. More preferably, this treatment is carried out together with one or a combination of the above-mentioned treatments.

The above-mentioned hydrophilic polymer chain is preferably poly(hydroxyethyl methacrylate). More preferably, the average molecular weight of poly(hydroxyethyl methacrylate) is 100,000 or more.

<Culture Method>

Next, a method of culturing cells using the culture chambers 1 shown in FIGS. 1 to 3 will be described.

The cell culture is performed by the following steps:
a) adding a medium in which cells are dispersed to the culture chambers 1;
b) culturing the cells;
c) replacing the medium;
d) allowing spheroids to grow;
e) suspending the spheroids in the medium; and
f) recovering the cells.

The above-mentioned steps can be classified into two steps, i.e., the step of culturing cells (cell culture step) and the step of recovering cells (cell harvesting step). The cell culture step includes the steps a) to d), and the cell harvesting step includes the steps e) and f).

The term "spheroid" used herein refers to a three-dimensional cell cluster including a number of aggregated cells.

Each of the steps will be described below.

a) Step of adding a medium in which cells are dispersed to the culture chambers 1

This step is a step of preparing for culture of cells. In this step, the total number of cells as described below are dispersed in a medium and are added to each culture chamber 1.

A lower limit of the total number of cells is equal to or greater than the number (n) of recesses 10 present in the culture chamber 1.

An upper limit of the total number of cells is equal to or less than a number obtained by multiplying the number (n) of recesses by a value obtained by dividing the volume (V) of each of the recesses 10 of the culture chamber 1 by the volume (v) of cells to be seeded. The upper limit of the total number of cells can be represented by the following formula using symbols: $V/v \times n$. This is based on the premise that the volumes (V) of the plurality of recesses 10 are the same. If the volumes (V) of the plurality of recesses 10 are different, an average value is used.

The medium is adjusted depending on the cells to be cultured.

b) Step of culturing cells

The cells are cultured for 12 hours or more in each culture chamber 1 to thereby allow the cells to form a spheroid. When the medium is added to each culture chamber 1, the cells dispersed in the medium are loaded into the recesses 10 and the cells are cultured in the respective recesses 10. It is preferable to load one cell into each recess 10, and it is preferable to form one spheroid in the space formed by the bottom portion 11. In each recess 10, a cell proliferates at the bottom portion 11 of the recess 10. If at least one cell is not present in each recess during culture and seeding, no spheroid is formed in the recess 10, because any cell does not move from the adjacent recess 10 to the said recess 10 during culture. In order to culture spheroids at a high density, it is preferable to form a spheroid in each recess 10. Accordingly, it is preferable to form at least one cell in each recess 10. In terms of the production efficiency, it is preferable to reduce the initial number of cells as much as possible and to recover as many spheroids as possible, and therefore it is preferable that the number of cells present in each recess 10 be small as much as possible. For this reason, it is preferable that one cell be present in each recess 10.

c) Step of replacing the medium

During replacement of the medium, 20% or more of the medium in each culture chamber 1 is sucked, and then the same amount of fresh medium is injected into the culture chamber. It is preferable to replace the medium at least once during cell culture. d) Step of allowing spheroids to grow The above-described steps a) to c) are performed a plurality of times to thereby allow spheroids to grow. In the case of differentiating and inducing spheroids, it is preferable that each spheroid be allowed to grow to a size limited by the space formed by the bottom portion 11 of each recess 10 and then the medium be replaced with differentiation induction medium to thereby differentiate each spheroid. In addition, it is more preferable that 60% or more of the total number of spheroids formed in the culture chambers 1 have a diameter in a range of ±5% of an average spheroid diameter.

e) Step of suspending the spheroids in the medium

After each spheroid is grown to a desired size, the cells cultured in each recess 11 are suspended in the medium by agitating the medium in each culture chamber 1. For example, this step is carried out by agitating the medium. Specifically, the agitation of the medium can be done by any one of the following means: (1) agitation of the medium by shaking each culture chamber 1; (2) agitation of the medium by sucking and discharging the medium (pipetting); (3) agitation of the medium by disposing a stirring blade in each culture chamber 1; (4) agitation of the medium by placing a stirrer in each culture chamber 1; and (5) agitation of the medium by a combination of two or more of the above-mentioned means (1) to (4).

f) Step of recovering the cells

The medium including the cells in each culture chamber 1 is sucked by a suction machine, to thereby recover the cells (spheroids) suspended in the medium.

As described above in the first embodiment, seeding of cells, replacement of a medium, and harvesting of cells can be performed in the same chamber, and in addition, spheroids can be recovered from each culture chamber.

Culture of cells using the culture chambers 1 of the first embodiment enables formation of a spheroid having a desired size on the bottom portion 11. Further, the cultured spheroids can be efficiently recovered. Specifically, the structure of each recess 10 including the bottom portion 11 and the opening portion 12 makes it possible to easily maintain a state in which cells adhering to the bottom portion 11 or being suspended in the medium are prevented from being removed when the medium is sucked during replacement of the medium. Thus, it can be expected that the removal of cells from the bottom portion 11 is suppressed. On the other hand, during the harvesting of cells, when the medium in the bottom portion 11 is sucked and discharged, it can be expected that the medium is allowed to easily flow through the opening portion 12. It can also be expected that the use of the hemispherical shape of the bottom portion 11 contributes to the formation of spheroids with a uniform shape and size.

Second Embodiment

While an example of the structure in which the bottom portion 11 has a hemispherical shape has been described in the first embodiment, other shapes of the bottom portion will be described in a second embodiment. The bottom portion may have any form, such as a shape formed using a part of a spherical shape, a truncated cone shape, or a linear shape. The linear shape of the bottom portion is a form having no substantial bottom portion and having a recess formed only by an opening portion. FIGS. 4 to 7 show examples of the shape of each recess according to this embodiment. FIGS. 4 to 7 show recesses 20A to 20D having bottom portions 21A to 21D, respectively, which are different from the bottom portion 11 of the first embodiment. Since the opening portion 12 can be formed with the same shape as that of the first embodiment, FIGS. 4 to 7 show examples of the shape of each recess in which the opening portions having the same shape are combined.

Figure 4:
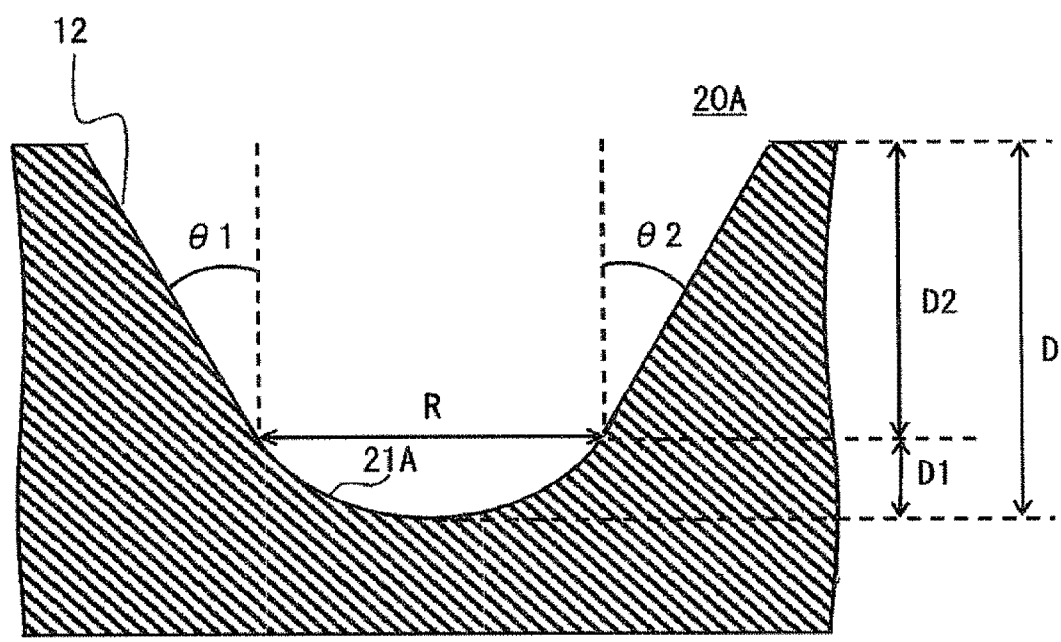
FIG. 4 is a diagram showing an example of the shape of a recess formed using a part of a spherical shape according to a second embodiment.
Figure 5:
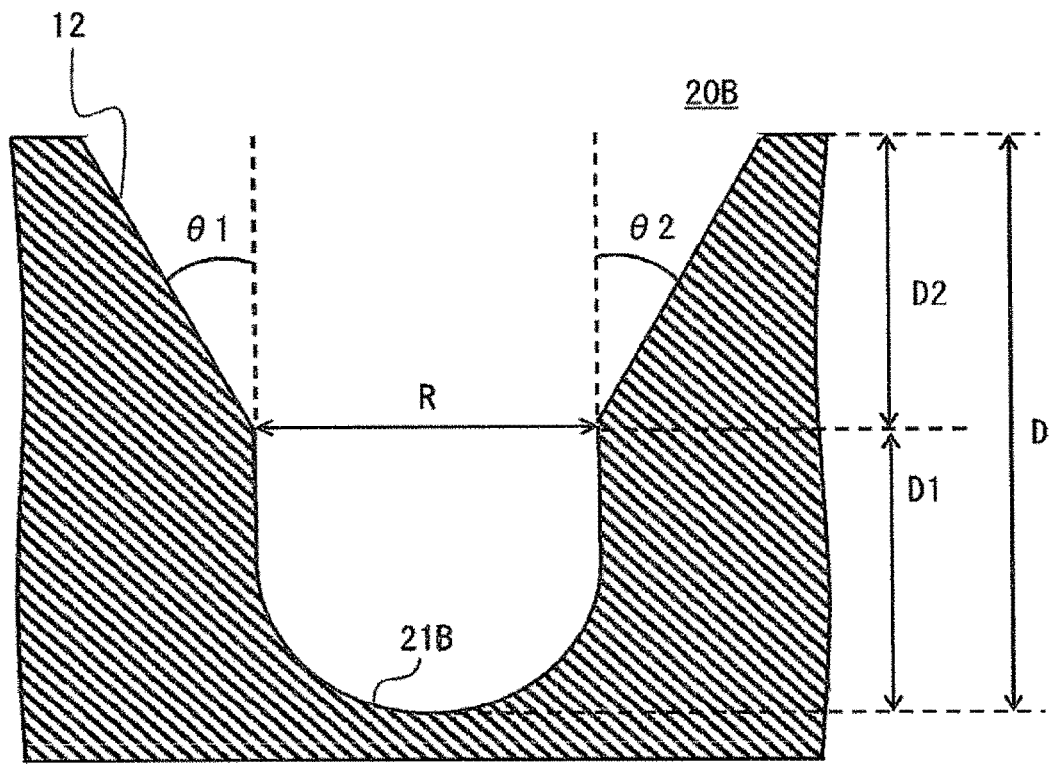
FIG. 5 is a diagram showing another example of the shape of a recess formed using a part of a spherical shape according to the second embodiment.

While in the first embodiment, a hemispherical shape, which is a shape obtained by dividing a spherical shape into halves, is used for the bottom portion 11, FIGS. 4 and 5 show examples in which different hemispherical shapes are used for the bottom portion. FIG. 4 shows the bottom portion 21A for which a portion less than a half of a spherical shape is used. In other words, FIG. 4 shows a case where a part of a hemispherical shape is used for the bottom portion 21A.

FIG. 5 shows the bottom portion 21B having a cylindrical shape with a hemispherical bottom. In the case of the shape of the bottom portion 21B shown in FIG. 5, as the length of the cylindrical portion increases, the cells are less likely to be suspended into the medium from the bottom portion 21B during harvesting of the cells. Accordingly, it is preferable to adjust the length of the cylindrical portion. For example, it is preferable to form the bottom portion 21B and the opening portion 12 so as to maintain the same ratio (1:1) between the depth (height) of the bottom portion 21B and the depth (height) of the opening portion 12.

Figure 6:
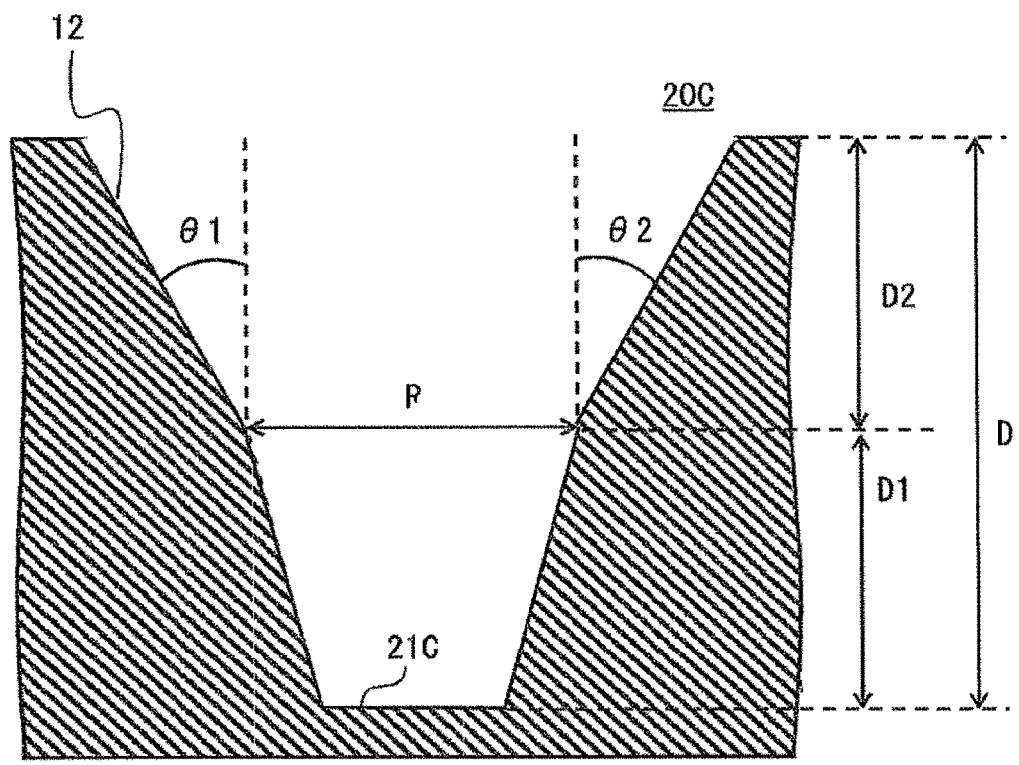
FIG. 6 is a diagram showing an example of the shape of a recess formed using a truncated cone shape according to the second embodiment.

FIG. 6 shows the bottom portion 21C for which a truncated cone shape is used. When the bottom portion is flat, the reflection and interference of light can be reduced, and thus it is useful for observation with a microscope.

Figure 7:
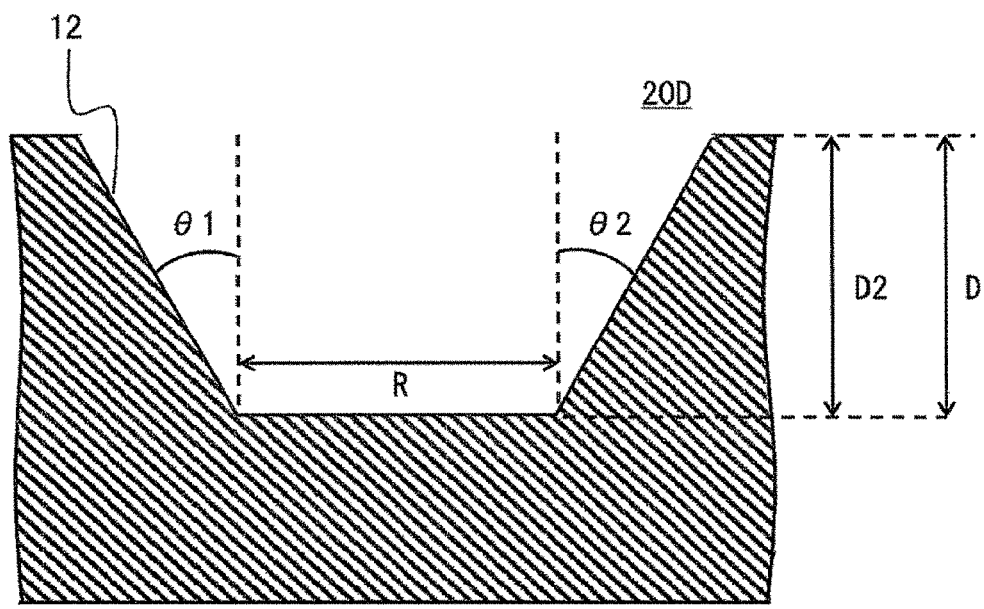
FIG. 7 is a diagram showing another example of the shape of a recess according to the second embodiment.

FIG. 7 shows an example of the shape of the recess 20D in which the bottom portion 21D has a linear shape, i.e., the bottom portion 21D does not form a space. The efficiency of culture and harvesting of cells in the recess 20D is lower than that of culture chambers having other shapes. However, the recess 20D has an advantage in facilitating the production process for the culture chambers.

A case where the opening portion 12 is formed with a shape similar to that of the first embodiment has been described in this embodiment. However, the present invention is not limited to this case.

The method of culturing cells using the culture chambers according to this embodiment is similar to that of the first embodiment, and thus the description thereof is omitted.

The culture chambers according to this embodiment can provide the same advantageous effects as those of the first embodiment.

Third Embodiment

Figure 8:
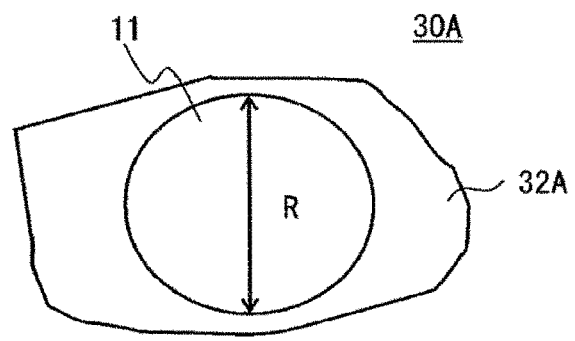
FIG. 8 is a diagram showing an example of the shape of an opening portion according to a third embodiment.
Figure 9:
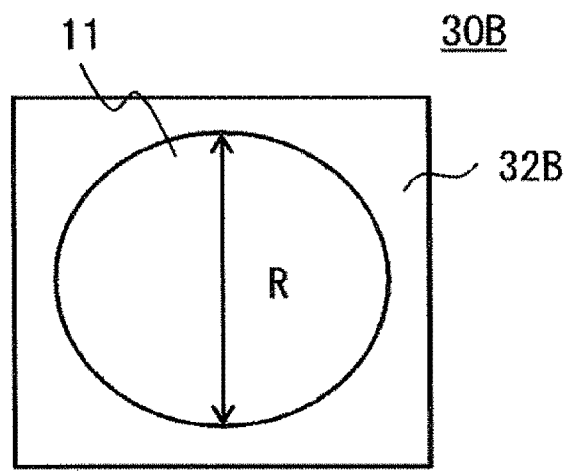
FIG. 9 is a diagram showing another example of the shape of an opening portion according to the third embodiment.

A mode in which the shape of the opening portion 12 is a circular shape or a substantially circular shape has been described in the above embodiments. A culture chamber including opening portions each having a shape other than a circular shape or a substantially circular shape will be described. An end of each opening portion may have a shape other than a circular shape or a substantially circular shape, such as a hemispherical shape, a trapezoidal shape, or an inverted triangular shape. On the other hand, it is necessary that the shape of the boundary where the opening portion contacts the bottom portion (the boundary portion of the opening portion) be the same as the shape of the boundary portion of the bottom portion. FIGS. 8 and 9 show recesses 30A and 30B, respectively, each having an end with a shape different from that of the opening portion 12 of the first embodiment. While FIGS. 8 and 9 show the same bottom portion 11 as that of the first embodiment, a combination of any of the bottom portions 21A to 21D of the second embodiment, or a bottom portion having another shape may be used. The bottom portion and the opening portion may have any shape as long as an inclined surface can be formed continuously at the boundary between the bottom portion and the opening portion.

FIG. 8 shows an example of the shape of an end of the opening portion 32A that is formed in a curve. FIG. 8 is a top view of the recess 30A. An end of the bottom portion 11 is indicated by a circle having the equivalent diameter R, and the outer periphery of the opening portion 32A is indicated by a curve. The end of the opening portion 32A has a curved shape which is not symmetric in the horizontal direction and the vertical direction. However, the end of the opening portion 32A may have a shape which is symmetric in the horizontal direction or the vertical direction. FIG. 9 shows an example in which an end of the opening portion 32B has a rectangular shape. Although FIG. 9 shows an example in which an end of the opening portion has a square shape, the end of the opening portion may have another polygonal shape, or a combination of a curve and a straight line. FIG. 9 is a top view of the recess 30B. The end of the bottom portion 11 is indicated by a circle having the equivalent diameter R, and the outer periphery of the opening portion 32B is indicated by a solid square. For example, the shape of the end of the bottom portion may be modified so as to adjust the area of the space between the end of the bottom portion and the adjacent recess. Since it is necessary for the shape of the end of the opening portion to play a role of promoting the suspension of cells, the taper angle is important.

In the shape examples shown in FIGS. 8 and 9, the taper angle has a value that varies depending on the shape of the opening portions 32A and 32B. This is because the inclination of the inclined surface that forms the wall varies depending on the shape of the opening portions 32A and 32B.

Each of the shapes of the opening portions illustrated in this embodiment can be combined with the shape of the bottom portion 11 described in the first embodiment, or the shape of the bottom portion described in the second embodiment. In addition, these shapes can also be combined with a shape other than the shapes of the bottom portion illustrated in the above embodiments, as a matter of course.

The method of culturing cells using the culture chambers according to this embodiment is similar to that of the first embodiment, and thus the description thereof is omitted.

The culture chambers according to this embodiment can provide the same advantageous effects as those of the first embodiment.

Fourth Embodiment

Figure 10:
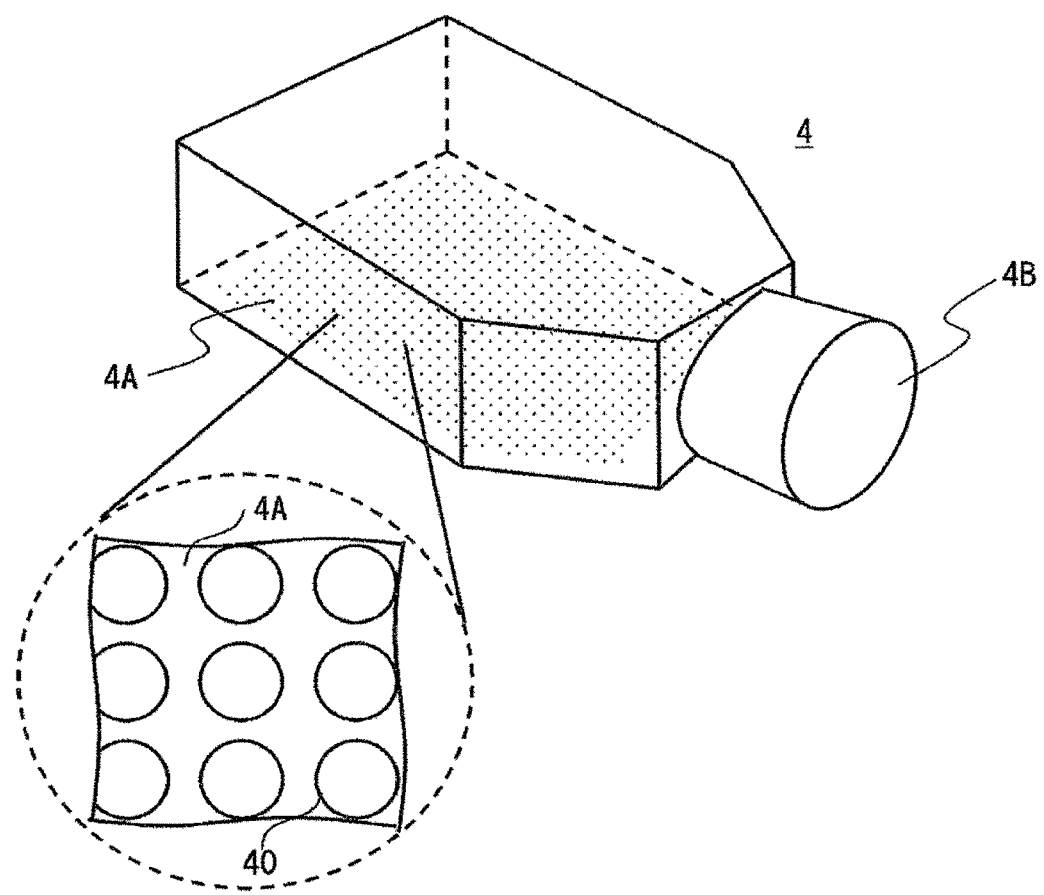
FIG. 10 is a diagram showing an example of the structure of a culture chamber according to a fourth embodiment.
Figure 11:
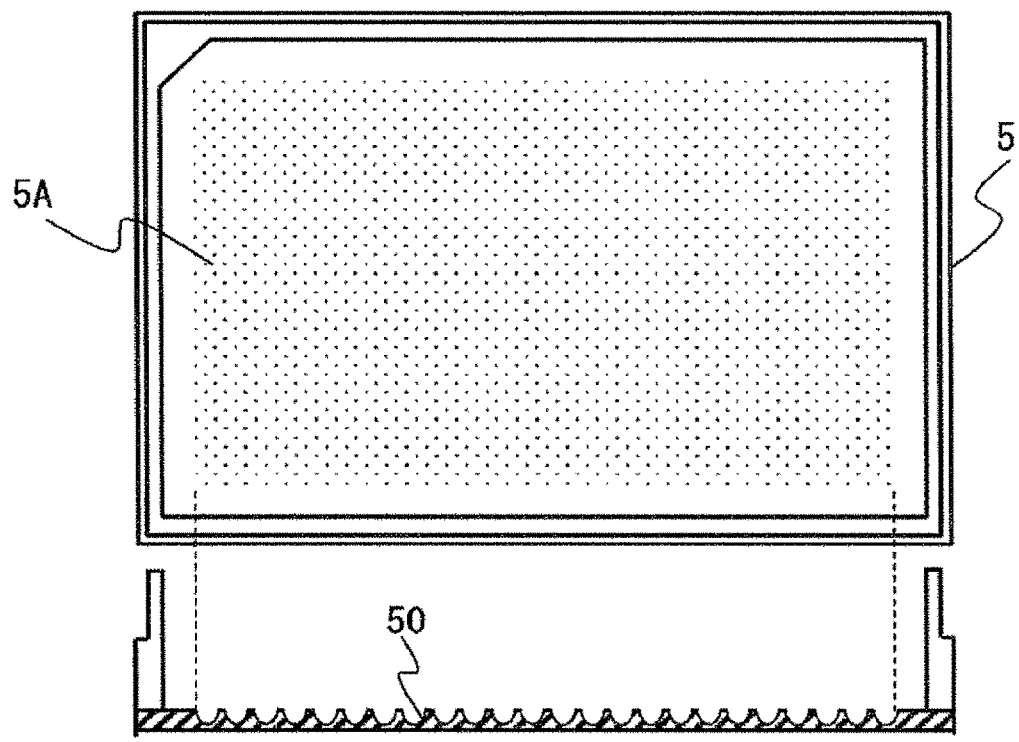
FIG. 11 is a diagram showing another example of the structure of the culture chamber according to the fourth embodiment.
Figure 12:
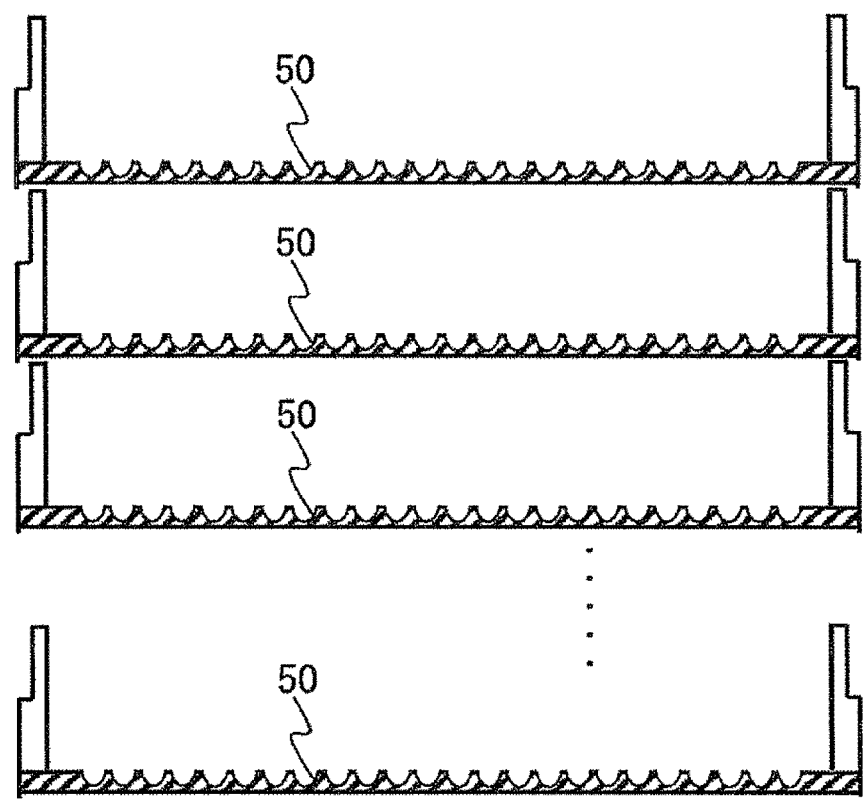
FIG. 12 is a diagram showing still another example of the structure of the culture chamber according to the fourth embodiment.

FIG. 1 illustrates a mode in which the culture chambers 1 according to one embodiment are arranged in the culture plate 3 (well plate). The culture chambers 1 according to one embodiment can also be formed in a chamber (instrument) other than the culture plate 3 shown in FIG. 1. FIGS. 10 to 12 show examples of the structure of a culture chamber according to a fourth embodiment. FIG. 10 is a schematic view showing an example of the structure in which a flask-shaped culture flask is used. FIG. 11 is a schematic view showing an example of the structure in which a frame of a culture plate is used. FIG. 12 is a schematic view showing an example of the structure in which the culture plate shown in FIG. 11 is designed in a stack shape and used.

In FIG. 10, a bottom surface of a culture flask 4 is used as a culture surface 4A (culture bottom surface). The culture surface 4A corresponds to each culture chamber 1 shown in FIG. 1. Accordingly, the culture surface 4A can also be referred to as a culture chamber. Like each culture chamber 1 shown in FIG. 1, the culture surface 4A is a unit for using the same medium. The culture flask 4 includes a cap 4B. The area of the culture surface 4A can be designed depending on the intended use. Examples of the size of a typical culture flask include 25, 75, and 225 $cm^2$. A plurality of recesses 40 are formed in the culture surface 4A of the culture flask 4. For example, in the bottom surface of the culture flask 4, a shaded area is designed as the culture surface 4A and the plurality of recesses 40 are formed in the culture surface 4A. The shape of each recess 40 (the shape of each of the bottom portion and the opening portion) may be any one of the shapes illustrated in the above embodiments.

FIG. 11 shows an example in which only the frame of a culture plate is used. In FIG. 1, the culture chambers 1 (wells) are formed in the culture plate 3, whereas in FIG. 11, a bottom surface of a culture plate 5 is used as a culture surface 5A (culture bottom surface). The culture surface 5A corresponds to each culture chamber 1 shown in FIG. 1. Accordingly, the culture surface 5A can also be referred to as a culture chamber. The culture surface 5A is a unit for using the same medium. The lower part of FIG. 11 shows an example (schematic cross-sectional view) of the structure of the culture surface 5A. For example, in the bottom surface of the culture plate 5, a shaded area is designed as the culture surface 5A and a plurality of recesses 50 are formed in the culture surface 5A. The recesses 50 shown in FIG. 11 are schematically illustrated. The number, size, and the like of the recesses 50 are designed depending on the intended use. The shape of each recess 50 (the shape of each of the bottom portion and the opening portion) may be any one of the shapes illustrated in the above embodiments.

FIG. 12 shows a structural example of a cell stack form in which a plurality of culture plates 5 shown in FIG. 11 are stacked. In other words, FIG. 12 shows an example of a multi-stage structure. In a case where cells are cultured in a closed system with a larger area, the cell stack form is generally used. While FIG. 12 illustrates an example in which the culture plates 5 shown in FIG. 11 are stacked, the culture plates 3 shown in FIG. 1 may be stacked. In FIG. 12, the illustration of a chamber that accommodates the plurality of stacked culture chambers and provides a mechanism for replacement of a medium is omitted. For example, a culture chamber having a typical stack shape can be used as the chamber that accommodates the plurality of culture plates. The explanation thereof is herein omitted.

Other Embodiments

In the above embodiments, the boundary between the bottom portion and the opening portion is defined to be parallel to the bottom of each culture chamber. However, it is not necessary that the boundary be parallel to the bottom. For example, the boundary may be inclined with respect to the bottom, or may be formed in a curve. It is only necessary that a sufficient space to form a spheroid can be formed in the bottom portion 11.

[Example]

As for a culture chamber for culturing a cell aggregate and a harvesting method thereof, experiments were conducted according to the following example and comparative example.

(1) Culture Chamber

Culture chambers shown in Table 1 were used.

TABLE 1

|  | Example | Comparative Example |
|---|---|---|
| Chamber | A culture place in which patterns of shapes shown in FIGS. 1 to 3 are arranged in a culture bottom surface was prepared. | EZ-Sphere ® (manufactured by ASAHI GLASS CO., LTD.) |
| Bottom shape of micro-chamber | hemispherical shape | spherical shape |
| The number of micro-spaces/wells | 600 | 578 |
| Taper angle | 10 degrees | There is no portion at which a taper angle is formed. |
| Equivalent diameter R | 500 μm | 400-500 μm |
| Depth | 400 μm (0.8 R) | 150-200 μm |
| Surface | p-HEMA | a product with a surface on which a cell non-adhesion treatment is performed |
| Shape of chamber | 24-well plate | 24-well plate |

As the culture chamber of the example, a culture plate in which wells (culture chambers 1) each including the recesses 10 shown in FIGS. 1 to 3 are formed was prepared.

In Table 1, microchambers respectively correspond to the recesses 10 shown in FIGS. 1 to 3 and each of micro-spaces is a space formed by each recess 10 (micro-space). It can be said that the number of micro-spaces per well is the number of recesses per well.

(2) Culture Method

To calculate a survival rate and a harvesting rate, which are described later, by image analysis, endodermal cells labeled with fluorescence of GFP were used. The endodermal cells, vascular endothelial cells, and human mesenchymal stem cells were mixed at a ratio of 10:5-10:2, and the cells were cultured for 30 days in an endothelial cell medium kit-2: EGM-2 BulletKit (product code CC-3162: Lonza). The medium was replaced once every two days.

(3) Measurement of the Survival Rate of Spheroids

All the wells were observed with a confocal laser microscope, and spheroids were recognized by image analysis software. Then, the number of the recognized spheroids was counted and the number was determined as the number of spheroids. The survival rate of spheroids was calculated by the following expression.

Spheroid survival rate (%)=(the number of spheroids)×100/(the number of micro-spaces)

A few hours after the cells were seeded (0th day), a spheroid-like cluster was formed in 90% or more of the micro-spaces in all the culture chambers. A value obtained by dividing the number of spheroids obtained after replacement of the medium on the 10th and 20th days of the culture by the number of spheroids obtained on the 0th day was determined as the survival rate of spheroids.

(4) Harvesting Method

After completion of the culture, the solution was agitated with a pipette (manufacturer, model number), and the suspended spheroids were recovered. For example, a pipette capable of sucking 1 mL of medium at maximum is suitably used for a 24-well plate that contains 500 μL to 1 mL of medium.

(5) Harvesting Efficiency

Before and after the harvesting of spheroids, images of the spheroids were taken by a confocal laser microscope.

(6) Results

Figure 13:
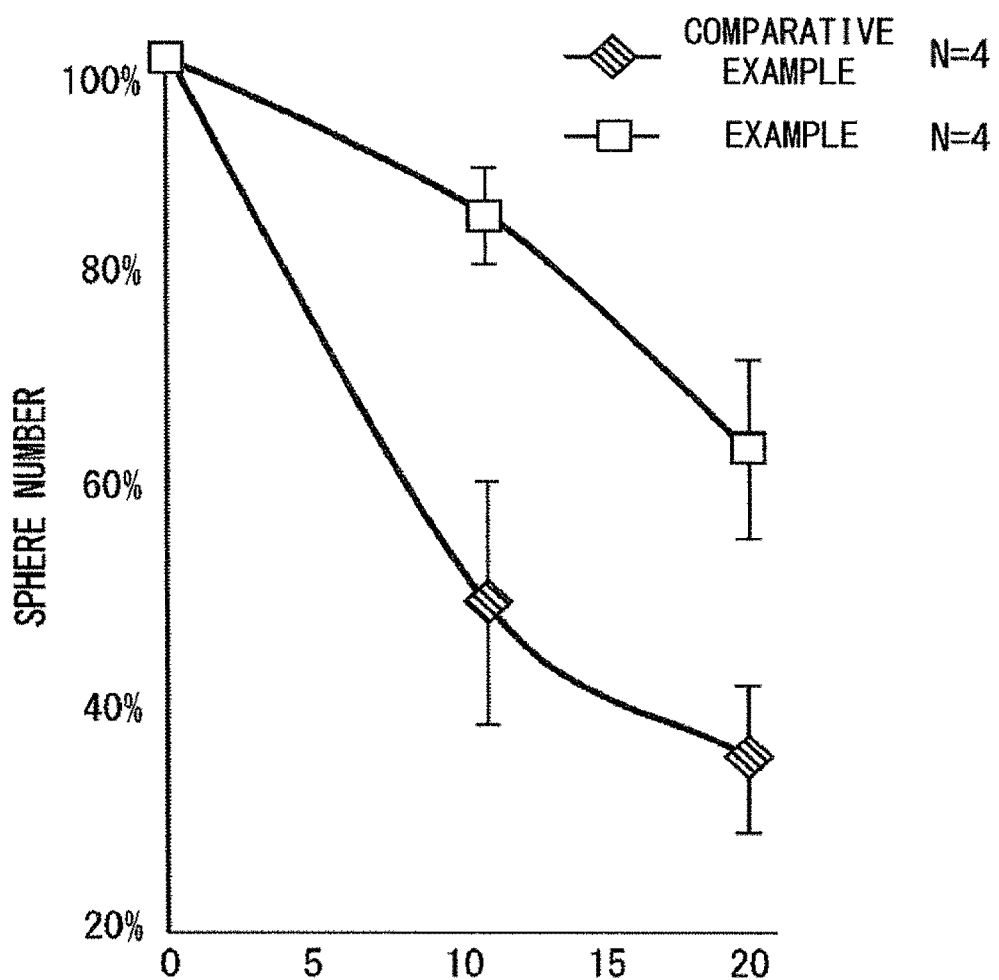
FIG. 13 is a diagram showing a survival rate of spheroids in an example and a survival rate of spheroids in a comparative example at the time of replacement of a medium.

FIG. 13 shows the survival rate of spheroids during replacement of the medium. The vertical axis represents the survival rate of spheroids (Sphere Number) and the horizontal axis represents the number of days of culture.

FIG. 13 shows data obtained from the start of culture to the 20th day of culture. As shown in FIG. 13, the survival rate of spheroids in the comparative example significantly decreased in comparison to that in the example. After culture for 20 days, the survival rate of spheroids in the example was 60% or more. This indicates that the survival rate of spheroid in the example was improved 1.5 times as high as that in the comparative example.

Figure 14:
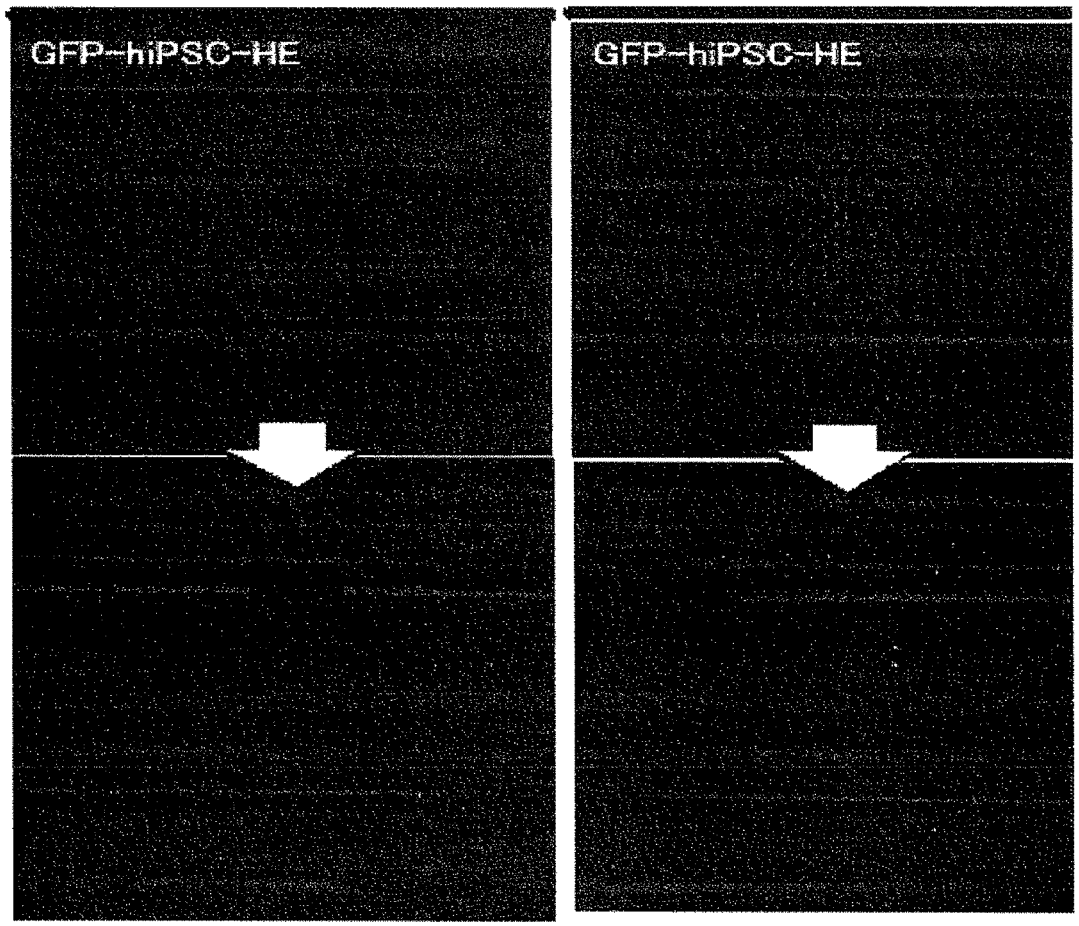
FIG. 14 shows a photograph illustrating an image of spheroids in the example and a photograph illustrating an image of spheroids in the comparative example before and after the replacement of a medium.

FIG. 14 shows the images of spheroids obtained before and after replacement of the medium in the example and the comparative example. FIG. 14 shows the images of spheroids in the culture chamber before and after the second replacement of the medium on the fourth day of culture. The left side of FIG. 14 shows a photograph of the example (Kuraray p-HEMA), and the right side of FIG. 14 shows a photograph of the comparative example (Iwaki MPC). The upper part of the figure shows images taken before replacement of the medium, and the lower part (below an arrow) of FIG. 14 shows images taken after replacement of the medium. More specifically, the images in the lower part of FIG. 14 show the state after replacement of the medium was performed twice, i.e., half of the medium was replaced (replacement of half of the medium), from the state before replacement of the medium.

In the images, white dots correspond to spheroids. Before replacement of the medium, spheroids are confirmed over the entire area. After replacement of the medium, in the example, there is no large difference in the number of spheroids before and after replacement of the medium and almost all the spheroids survived, whereas in the comparative example, only about a half of the spheroids were survived.

Figure 15:
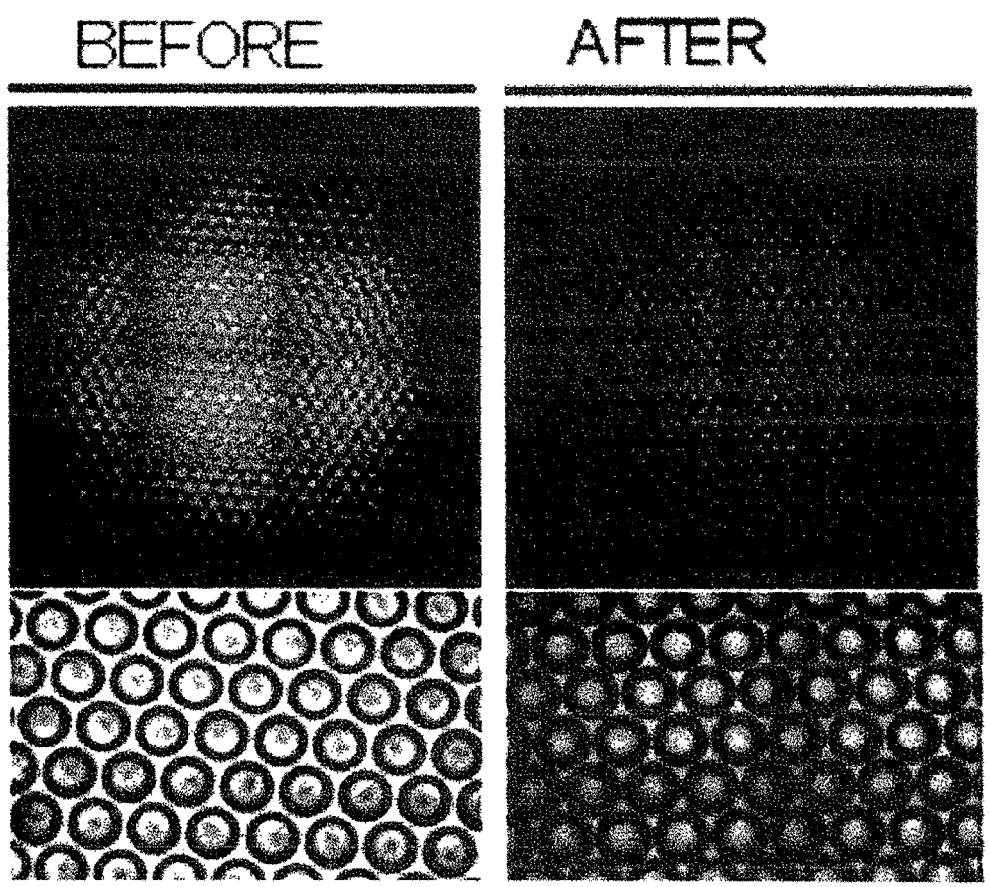
FIG. 15 shows a photograph illustrating an image of cells before the cells are recovered in the example and a photograph illustrating an image of cells after the cells are recovered in the example.
Figure 16:
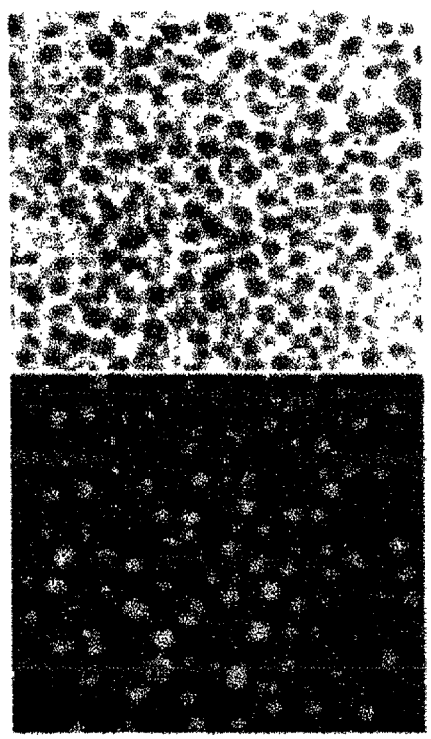
FIG. 16 shows photographs of spheroids recovered from a culture chamber according to the example.

FIG. 15 shows images taken before and after the harvesting of cells in the example. The left side (BEFORE) in FIG. 15 shows the image of cells taken before the harvesting of cells, and the right side (AFTER) in FIG. 15 shows the image of cells taken after the harvesting of cells. The upper part of FIG. 15 shows the image of the entire culture chamber, and the lower part of FIG. 15 shows the enlarged image of a part of the culture chamber. FIG. 16 shows photographs of the spheroids recovered from the culture chamber according to the example.

Dot-like portions in each black circular microchamber (recess) correspond to spheroids. No dot-like portions are found in the image taken after the harvesting of cells, which indicates that almost 100% of the cells can be recovered. Further, as shown in FIG. 16, the recovered cells have an excellent spheroid shape, and each spheroid was not destroyed by the harvesting operation.

Note that the present invention is not limited to the embodiments described above. Those skilled in the art can easily make modifications, additions, and conversions on each component in the above embodiments within the scope of the present invention.

This application is based upon and claims the benefit of priority from Japanese patent application No. 2013-120915, filed on Jun. 7, 2013, the disclosure of which is incorporated herein in its entirety by reference.

REFERENCE SIGNS LIST

1 Culture Chamber
3, 5 CULTURE PLATE
4A, 5A CULTURE SURFACE
5 CULTURE FLASK
10, 20A-20D, 30A, 30B, 40, 50 RECESS
11, 21A-21D BOTTOM PORTION
12, 32A, 32B OPENING PORTION

The invention claimed is:

1. A culture chamber comprising:
a well or flask, the well or flask comprising a plurality of recesses formed in a bottom of the well or flask, each recess having a bottom portion and an opening portion, wherein:
the bottom portion of the recess comprises a hemispherical shape, a cylindrical shape with a hemispherical bottom, or a truncated cone shape,
each of the plurality of recesses comprises a cell non-adhesive surface on which a poly(hydroxyethyl methacrylate) is immobilized after a functional group is formed in the recesses by a surface modification treatment method selected from the group consisting of a coating, corona discharge, UV ozonation, and a combination thereof, and the treatment is performed so that a water contact angle becomes 45 degrees or less,
the opening portion of the recess is defined by a wall that surrounds an area from a boundary between the opening portion and the bottom portion of the recess to an end of each of the recesses, the wall comprising a taper angle of 10 to 20 degrees,
an equivalent diameter of the boundary is 50 μm to 2 mm and a depth from a bottom of the bottom portion to the end of each of the recesses is 0.6 or more times to 3 or less times of the equivalent diameter,
the wall defining the opening portion of the recess forms a surface continuous to the bottom portion of the recess, and an inclination of the surface continuous to the bottom portion changes as the taper angle of the wall of the opening portion is larger than a taper angle of the bottom portion at the boundary, and
an area between two adjacent recesses is flat and a distance between the two recesses is 5 μm to 50 μm.

2. The culture chamber according to claim 1, wherein the end of each of the recesses comprises one selected from the group consisting of a hemispherical shape, a trapezoidal shape, and an inverted triangular shape.

3. The culture chamber according to claim 1, wherein the culture chamber is a resin molding formed from one or a combination of two or more selected from the group consisting of an acrylic resin, a polylactic acid, a polyglycolic acid, a styrene resin, an acrylic styrene copolymer resin, a polycarbonate resin, a polyester resin, a polyvinyl alcohol resin, an ethylene vinyl alcohol copolymer resin, a thermoplastic elastomer, a vinyl chloride resin, and a silicon resin.

4. The culture chamber according to claim 1, wherein a phospholipid or a phospholipid-polymer complex is immobilized in the recesses.

5. The culture chamber according to claim 1, wherein an average molecular weight of the poly(hydroxyethyl methacrylate) is 100,000 or more.

6. The culture chamber according to claim 1, wherein the equivalent diameter of the boundary is 50 μm to 1 mm.

7. A method for cell seeding, cell culture, replacement of a medium, and harvesting of cells, comprising:
dispersing cells into a medium, a total number of the cells being equal to or greater than a number N of the recesses of the culture chamber according to claim 1 and equal to or less than a number obtained by multiplying the number N of the recesses by a value obtained by dividing a volume V1 of a space defined by each of the recesses by a volume V2 of cells to be seeded; and
adding the medium to the culture chamber.

8. The culture method according to claim 7, wherein one spheroid is formed in one space defined by each of the recesses.

9. The culture method according to claim 8, wherein the spheroid is allowed to grow.

10. The culture method according to claim 8, wherein the spheroid is differentiated and induced.

11. The culture method according to claim 7, wherein 60% or more of a total number of spheroids formed in the culture chamber have a diameter in a range of ±5% of an average spheroid diameter.

12. The culture method according to claim 7, wherein cells in the recesses are recovered by agitating the medium.

13. The culture method according to claim 12, wherein the agitation of the medium is done by one or more means selected from the group consisting of agitation of the medium by shaking the culture chamber; agitation of the medium by sucking and discharging the medium; agitation of the medium by disposing a stirring blade in the culture chamber; and agitation of the medium by placing a stirrer in the culture chamber.

14. The culture method according to claim 7, wherein the medium is replaced at least once, and 20% or more of the medium is replaced.

15. A culture method of cell seeding, cell culture, replacement of a medium, and harvesting of cells comprising:
dispersing cells into a medium, the number of cells being equal to or greater than a number n of recesses of the culture chamber according to claim 1 and equal to or less than a number obtained by multiplying the number n of the recesses by a value obtained by dividing a volume V of each of the recesses by a volume v of cells to be seeded, and adding the medium to the culture chamber;
culturing the cells in the culture chamber for 12 hours or more to form a spheroid;
sucking 20% or more of the medium and then injecting the same amount of fresh medium;
repeating the dispersing, the culturing and the sucking a plurality of times to allow the spheroid to grow;
allowing the spheroid to grow to a desired size and then agitating the medium to suspend the cells within the recesses in the medium; and
sucking the medium comprising the cells by a suction machine to recover the cells.

* * * * *

UNITED STATES PATENT AND TRADEMARK OFFICE
CERTIFICATE OF CORRECTION

PATENT NO. : 10,494,593 B2
APPLICATION NO. : 14/896251
DATED : December 3, 2019
INVENTOR(S) : Yoko Ejiri et al.

It is certified that error appears in the above-identified patent and that said Letters Patent is hereby corrected as shown below:

On the Title Page

On page 2, Column 2, item (56), other publications, Line 21, delete "reations" and insert -- reactions --, therefor.

On page 2, Column 2, item (56), other publications, Line 22, delete "speroids cultureed" and insert -- spheroids cultured --, therefor.

Signed and Sealed this
First Day of September, 2020

Andrei Iancu
*Director of the United States Patent and Trademark Office*